(12) United States Patent
Mou et al.

(10) Patent No.: US 10,969,322 B2
(45) Date of Patent: Apr. 6, 2021

(54) GAS DETECTING DEVICE

(71) Applicant: Microjet Technology Co., Ltd., Hsinchu (TW)

(72) Inventors: Hao-Jan Mou, Hsinchu (TW); Ching-Sung Lin, Hsinchu (TW); Chi-Feng Huang, Hsinchu (TW); Yung-Lung Han, Hsinchu (TW); Wei-Ming Lee, Hsinchu (TW)

(73) Assignee: MICROJET TECHNOLOGY, LTD., Hsinchu (TW)

( * ) Notice: Subject to any disclaimer, the term of this patent is extended or adjusted under 35 U.S.C. 154(b) by 208 days.

(21) Appl. No.: 16/277,426

(22) Filed: Feb. 15, 2019

(65) Prior Publication Data

US 2019/0331582 A1 Oct. 31, 2019

(30) Foreign Application Priority Data

Apr. 27, 2018 (TW) .................................. 107114585

(51) Int. Cl.
*G01N 15/06* (2006.01)
*F04B 43/04* (2006.01)
*G01N 33/00* (2006.01)
*G01N 15/00* (2006.01)

(52) U.S. Cl.
CPC ....... *G01N 15/0637* (2013.01); *F04B 43/046* (2013.01); *G01N 15/0656* (2013.01); *G01N 33/0067* (2013.01); *G01N 33/0073* (2013.01); *G01N 2015/0046* (2013.01)

(58) Field of Classification Search
CPC ........... G01N 15/0637; G01N 15/0656; G01N 33/0067; G01N 33/0073; F04B 43/046

USPC ....................................................... 73/28.01
See application file for complete search history.

(56) References Cited

U.S. PATENT DOCUMENTS

2017/0370809 A1* 12/2017 Miller-Lionberg ........................
G01N 1/2202

FOREIGN PATENT DOCUMENTS

| EP | 2905673 A2 | 8/2015 |
| TW | 201727068 A | 8/2017 |
| TW | M553417 U | 12/2017 |
| TW | M558353 U | 4/2018 |
| WO | WO 2008/024138 A1 | 2/2008 |
| WO | WO 2016/190957 A1 | 12/2016 |

* cited by examiner

*Primary Examiner* — Tarun Sinha
(74) *Attorney, Agent, or Firm* — Birch, Stewart, Kolasch & Birch, LLP

(57) ABSTRACT

A gas detecting device includes a main body, a gas sensing module, a particulate measuring module and a control module. A chamber is formed within the main body. The main body has a first inlet, a second inlet and an outlet in fluid communication with the chamber. The gas sensing module includes a compartment body, a carrying plate, a sensor and an actuator. The actuator introduces ambient gas into the gas sensing module through the first inlet, and the gas is measured by the sensor and discharged from the outlet of the compartment body. The particulate measuring module is disposed within the chamber of the main body and includes an inlet channel, an outlet channel and a particulate detector. The gas is introduced into the particulate measuring module through the inlet channel, and a concentration of particulates in the gas is measured by the particulate detector.

17 Claims, 17 Drawing Sheets

GAS DETECTING DEVICE

FIELD OF THE INVENTION

The present disclosure relates to a gas detecting device, and more particularly to a slim and portable gas detecting device for monitoring ambient gas.

BACKGROUND OF THE INVENTION

Nowadays, people pay much attention to the air quality in the environment. For example, it is important to monitor carbon monoxide, carbon dioxide, volatile organic compounds (VOC), Particulate Matter (PM2.5), nitric oxide, sulfur monoxide, and so on. Moreover, it is also important to monitor other particulate matters contained in the gas. The exposures of these substances in the environment will cause human health problems or even harm the life. Therefore, it is important for every country to monitor the air quality in the environment and help people escape or prevent from the injuries.

Generally, it is feasible to use a gas sensor to monitor the air quality in the environment. If the gas sensor is capable of immediately providing people with the monitored information relating to the environment for caution, it may help people escape or prevent from the injuries and influence on human health caused by the exposure of the substances described above in the environment. In other words, the gas sensor is suitably used for monitoring the ambient air in the environment.

Generally, portable devices are the mobile devices that are usually carried by the people when they go out. Therefore, people pay much attention to the portable device having a gas detecting module embedded therein. More particularly, the developing trend of the current portable device is light and slim while maintaining high performance. Therefore, it is important to reduce the thickness of the gas detecting module and assembly the gas detecting module in the portable device for application and utilization.

SUMMARY OF THE INVENTION

An object of the present disclosure is to provide a gas detecting device, which is a slim-type portable device. The gas detecting device includes a gas sensing module capable of monitoring the air quality in the environment at any time and includes an actuator actuated to guide the gas into the interior of the gas sensing module rapidly and stably, so that the efficacy of the gas sensing module is enhanced. Moreover, the actuator and a sensor of the gas sensing module are separated from each other by the compartments of a compartment body, the heat generated from the actuator is blocked to reduce the influence on the sensor while the sensor monitors the air quality. In such way, the monitoring accuracy of the sensor is not adversely affected by the heat and other components (e.g., the control module) within the gas detecting device. Consequently, the gas detecting device can monitor the air quality in the environment rapidly and accurately at anytime and anywhere. Furthermore, the gas detecting device further includes a particulate measuring module for measuring the concentration of the particulates in the gas from the external environment and providing an external connection device with the monitoring value. The external connection device can obtain the information carried by the monitoring value immediately and announce an alert to the user in the environment so that the user can take preventive measures or escape immediately, and the influence and injury to the human health caused by the gas exposure in the environment will be prevented.

In accordance with an aspect of the present disclosure, a gas detecting device is provided. The gas detecting device includes a main body, a gas sensing module, a particulate measuring module and a control module. The main body has a portable size defined by a length, a width and a height, and has a chamber, a first inlet, a second inlet and an outlet. The chamber is disposed in the interior of the main body and the first inlet, the second inlet and the outlet are in communication with the chamber. The gas sensing module includes a compartment body, a carrying plate, a sensor and an actuator. The compartment body is located under the first inlet of the main body. The compartment body has a partition plate, and the interior of the compartment body is divided into a first compartment and a second compartment by the partition plate. The partition plate has a notch for allowing the first compartment and the second compartment to be in fluid communication with each other. The first compartment has an opening, and the second compartment has an outlet aperture. The carrying plate is assembled on a bottom of the compartment body and is packaged on and electrically connected to the sensor. The sensor penetrates the opening and is disposed within the first compartment. The actuator is disposed within the second compartment, and the actuator and the sensor are separated from each other. The actuator is actuated to introduce ambient gas into the gas sensing module through the first inlet, and the gas is measured by the sensor and discharged from the outlet of the compartment body. The particulate measuring module is disposed within the chamber of the main body, and includes an inlet channel, an outlet channel and a particulate detector. The particulate detector is disposed within the particulate measuring module. The inlet channel is aligned with the second inlet of the main body. The outlet channel is aligned with the outlet of the main body. The gas is introduced into the particulate measuring module through the inlet channel, a concentration of particulates in the gas is measured by the particulate detector and the gas is discharged from the outlet channel. The control module controls the actuations and detecting operations of the gas sensing module and the particulate measuring module and converts the detection results of the gas sensing module and the particulate measuring module into a monitoring value to be stored and transmitted to an external connection device for storage.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

Figure 1A:
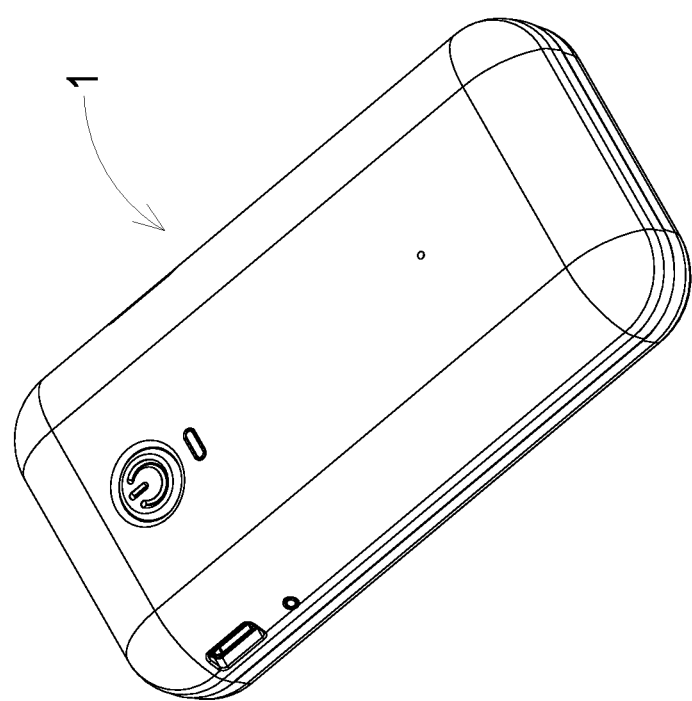
FIG. 1A is a schematic perspective view illustrating a gas detecting device according to an embodiment of the present disclosure.
Figure 1B:
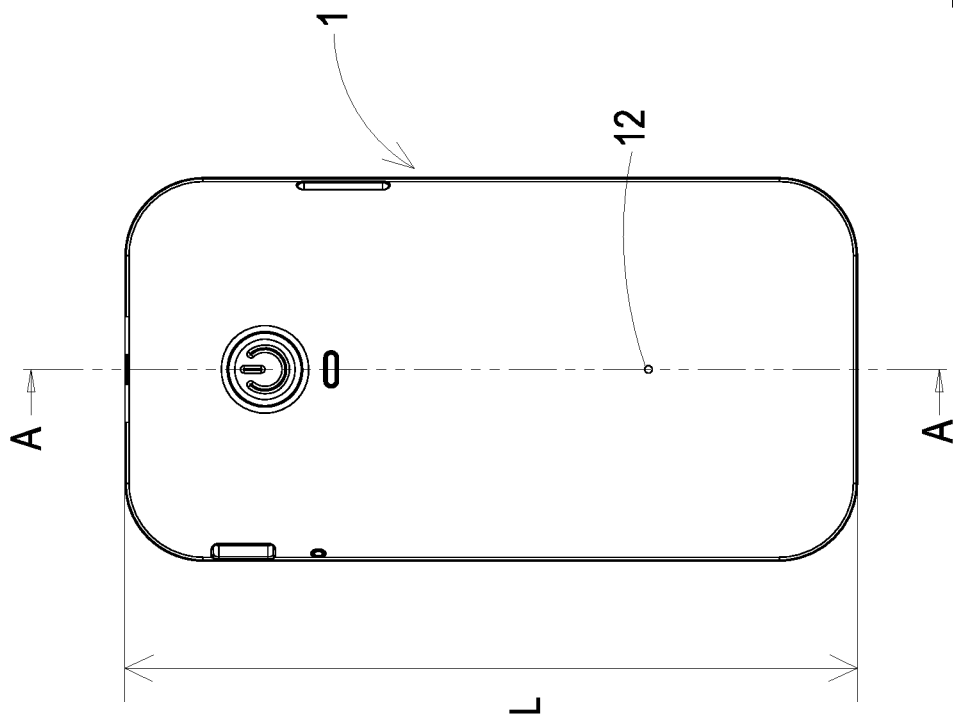
FIG. 1B is a schematic front view illustrating the gas detecting device of FIG. 1A.
Figure 1D:
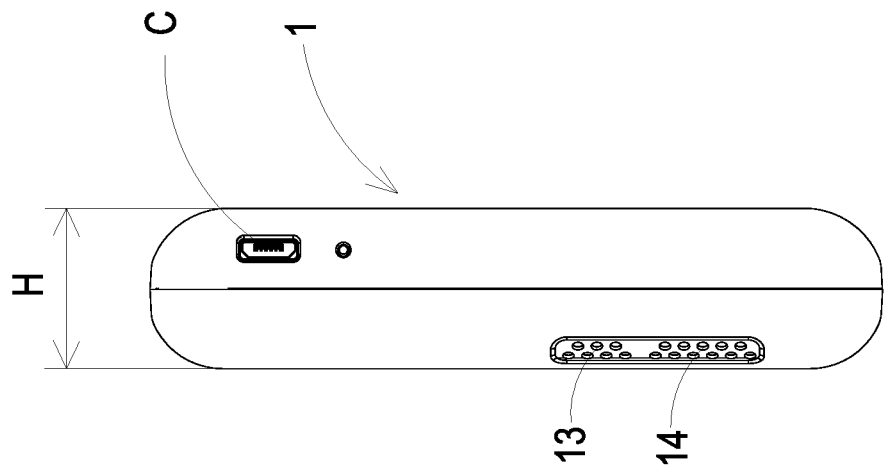
FIG. 1D is a schematic side view illustrating the gas detecting device of FIG. 1A.
Figure 1C:
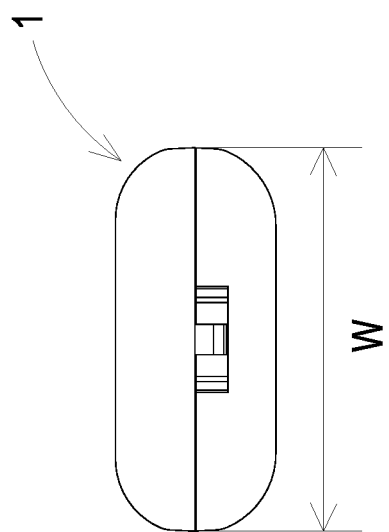
FIG. 1C is a schematic top view illustrating the gas detecting device of FIG. 1A.
Figure 2:
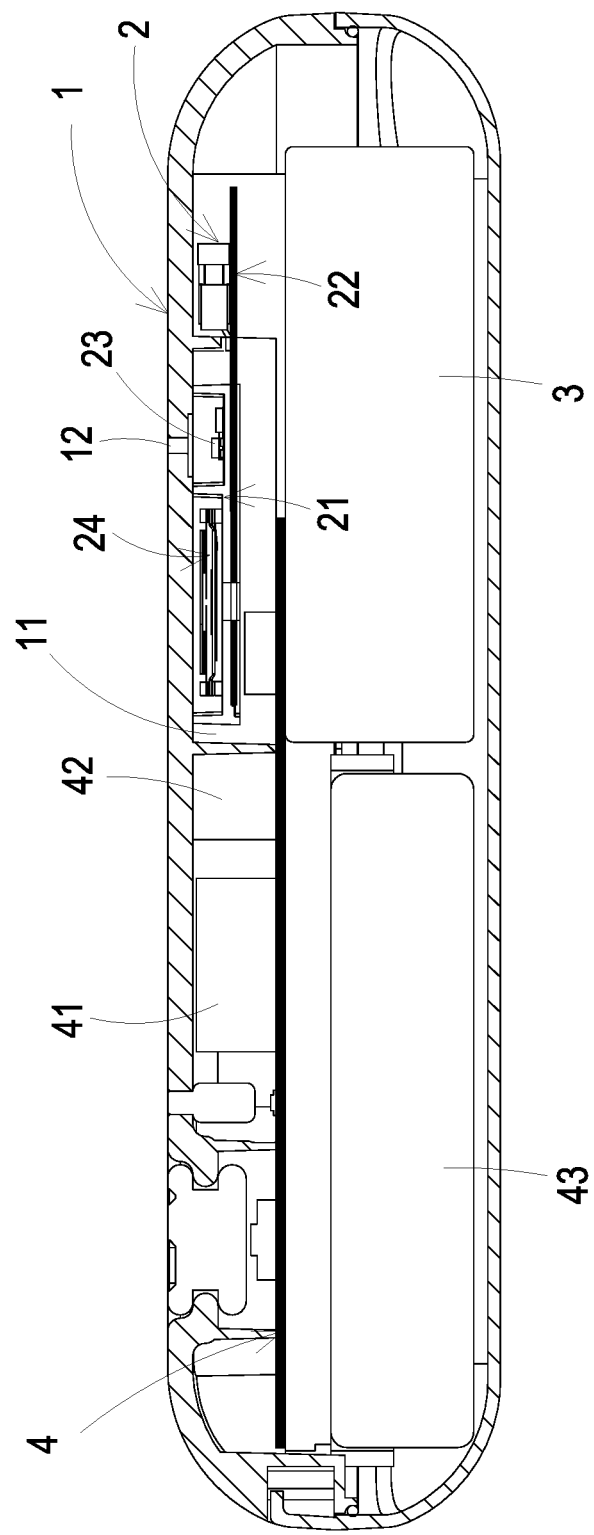
FIG. 2 is a schematic cross-sectional view illustrating the gas detecting device of FIG. 1B and taken along the line A-A.
Figure 3A:
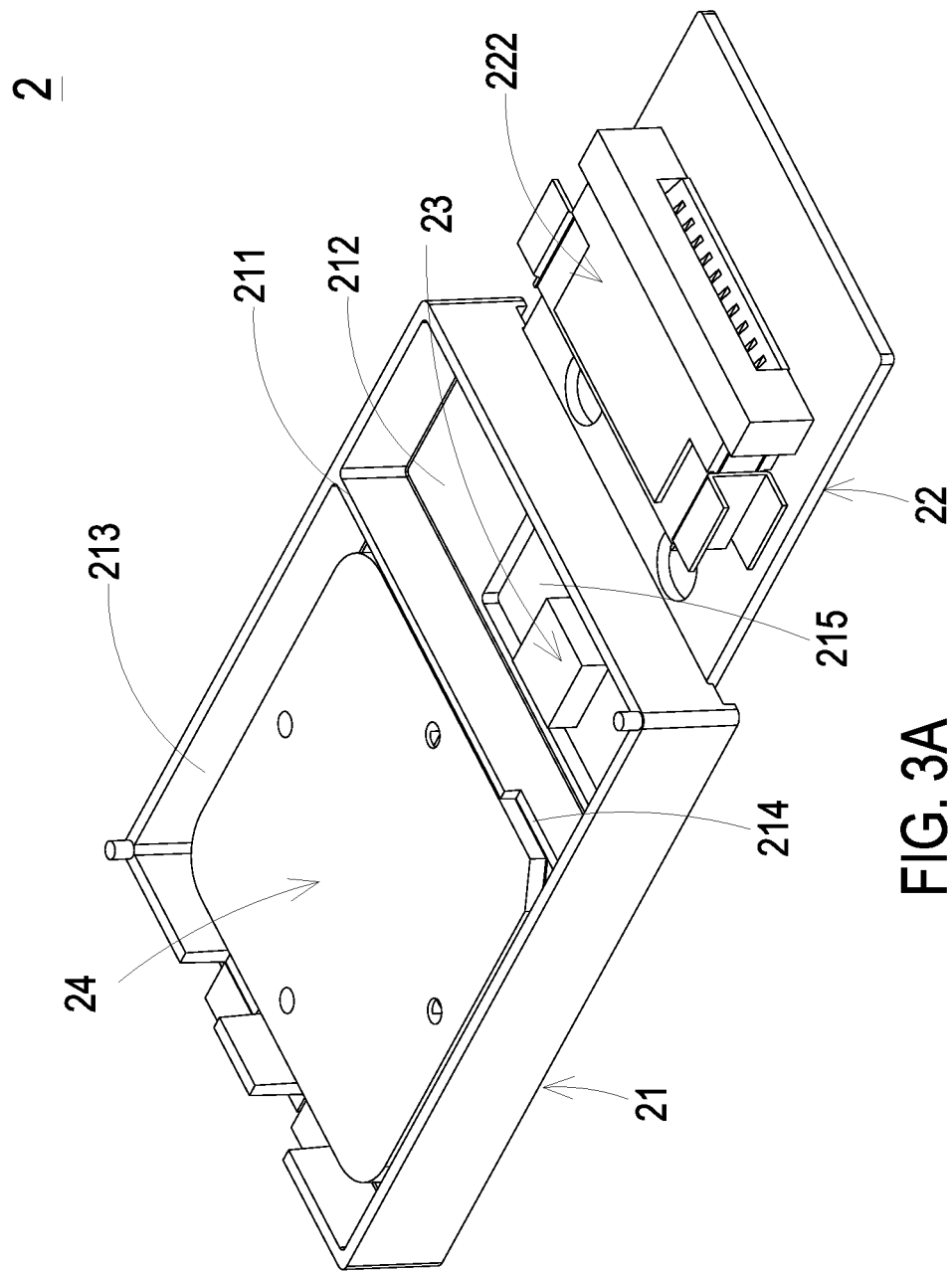
FIG. 3A is a schematic perspective view illustrating the gas sensing module of the gas detecting device according to the embodiment of the present disclosure and taken along the front side.
Figure 3B:
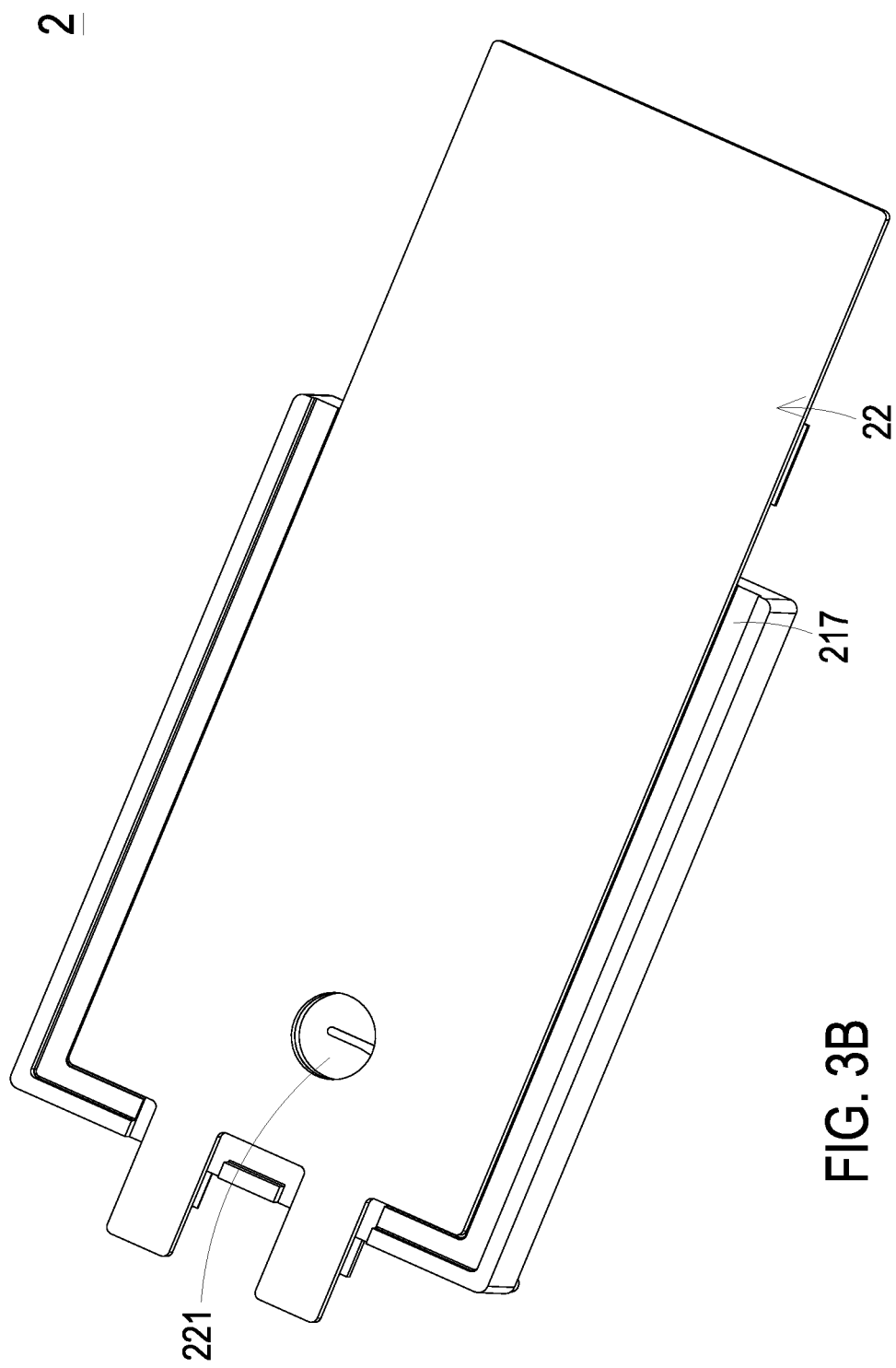
FIG. 3B is a schematic perspective view illustrating the gas sensing module of the gas detecting device according to the embodiment of the present disclosure and taken along the rear side.
Figure 3C:
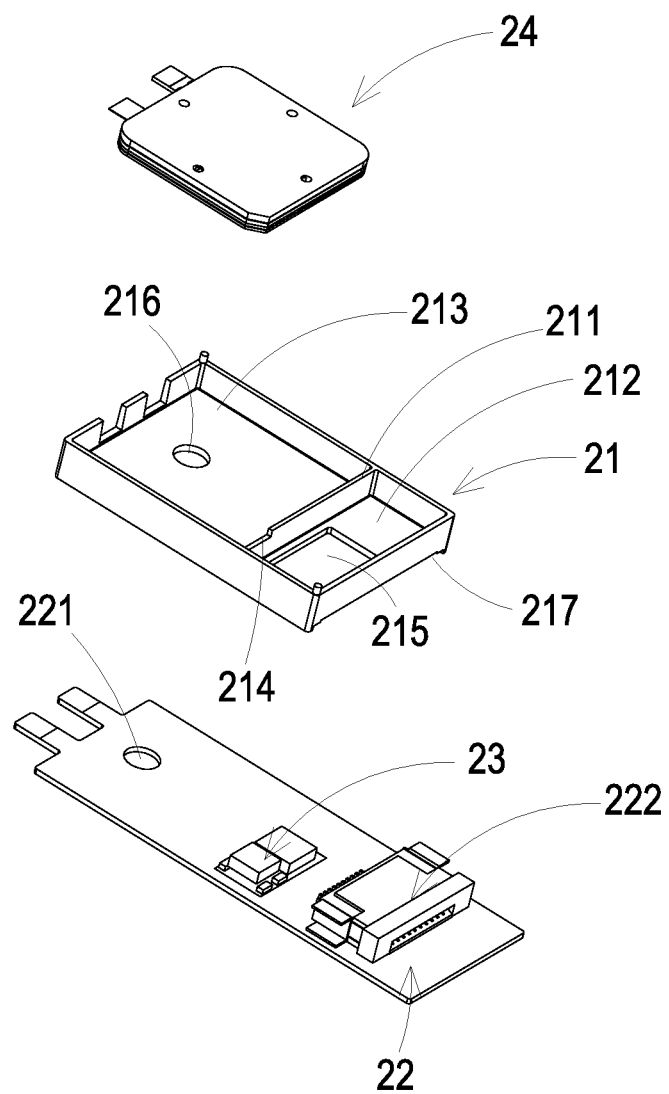
FIG. 3C is a schematic exploded view illustrating the gas sensing module of the gas detecting device according to the embodiment of the present disclosure.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIGS. 1 to 3C, FIG. 8 and FIG. 9. The present discourse provides a gas detecting device including at least one main body 1, at least one gas sensing module 2, at least one particulate measuring module 3, at least one control module 4, at least one length L, at least one width W, at least one height H, at least one chamber 11, at least one first inlet 12, at least one second inlet 13, at least one outlet 14, at least one compartment body 21, at least one carrying plate 22, at least one sensor 23, at least one actuator 24, at least one partition plate 211, at least one first compartment 212, at least one second compartment 213, at least one notch 214, at least one opening 215, at least one outlet aperture 216, at least one inlet channel 31, at least one outlet channel 32, at least one particulate detector, at least one monitoring value and at least one external connection device 5. The number of the main body 1, the gas sensing module 2, the particulate measuring module 3, the control module 4, the length L, the width W, the height H, the chamber 11, the first inlet 12, the second inlet 13, the outlet 14, the compartment body 21, the carrying plate 22, the sensor 23, the actuator 24, the partition plate 211, the first compartment 212, the second compartment 213, the notch 214, the opening 215, the outlet aperture 216, the inlet channel 31, the outlet channel 32, the particulate detector, the monitoring value and the external connection device 5 is exemplified by one for each in the following embodiments but not limited thereto. It is noted that each of the main body 1, the gas sensing module 2, the particulate measuring module 3, the control module 4, the length L, the width W, the height H, the chamber 11, the first inlet 12, the second inlet 13, the outlet 14, the compartment body 21, the carrying plate 22, the sensor 23, the actuator 24, the partition plate 211, the first compartment 212, the second compartment 213, the notch 214, the opening 215, the outlet aperture 216, the inlet channel 31, the outlet channel 32, the particulate detector, the monitoring value and the external connection device 5 can also be provided in plural numbers.

Please refer to FIGS. 1A to 1D and FIG. 2. The present disclosure provides a gas detecting device. The gas detecting device includes a main body 1, a gas sensing module 2, a particulate measuring module 3 and a control module 4. In order to make the gas detecting device slim and portable, the structure of the gas detecting device is specially designed to be held easily, less prone to slip off the grasp, and carried around conveniently for the user. In this embodiment, the main body 1 may be a thinned cuboid body with a portable size. The portable size is defined by a length L, a width W and a height H. The gas sensing module 2, the particulate measuring module 3 and the control module 4 are disposed in the main body 1 by an optimal arrangement manner. The size of the main body 1 is specially designed as follows so as to achieve the optimal arrangement: the length L of the main body 1 is in the range between 92 mm and 102 mm, the width W of the main body 1 is in the range between 41 mm and 61 mm, and the height H of the main body 1 is in the range between 19 mm and 23 mm. Preferably, the length L is 97 mm, the width W is 51 mm, and the height H is 21 mm. Consequently, the gas detecting device is held easily, less prone to slip off the grasp, and carried around conveniently for the user. Moreover, a chamber 11 is formed in the interior of the main body 1. The main body 1 has a first inlet 12, a second inlet 13 and an outlet 14, which are in fluid communication with the chamber 11.

Please refer to FIG. 2 and FIGS. 3A to 3C, the gas sensing module 2 is disposed in the chamber 11. In this embodiment, the gas sensing module 2 includes a compartment body 21, a carrying plate 22, a sensor 23 and an actuator 24. The compartment body 21 is located under the first inlet 12 of the main body 1. The compartment body 21 includes a partition plate 211, and the interior of the compartment body 21 is divided into a first compartment 212 and a second compartment 213 by the partition plate 211. The partition plate 211 has a notch 214 for allowing the first compartment 212 and the second compartment 213 to be in fluid communication with each other. The first compartment 212 has an opening 215. The second compartment 213 has an outlet aperture 216. The bottom of the compartment body 21 has an accommodation recess 217. The accommodation recess 217 allows the carrying plate 22 to be partially received and positioned therein, so that the bottom of the compartment body 21 is covered by the carrying plate 22. The edge of the bottom of the compartment body 21 is sealed by the carrying plate 22. The carrying plate 22 has an opening 221. The sensor 23 is packaged on and electrically connected to the carrying plate 22. In such way, the carrying plate 22 is assembled on the bottom of the compartment body 21. The opening 221 is aligned with the outlet aperture 216 of the second compartment 213. The sensor 23 penetrates the opening 215 of the first compartment 212 and is disposed within the first compartment 212 for measuring the gas within the first compartment 212. The actuator 24 is disposed within the second compartment 213. Since the actuator 24 in the second compartment 213 and the sensor 23 in the first compartment 212 are separated from each other by the partition plate 211, the heat generated from the actuator 24 is blocked by the partition plate 211 while the actuator 24 is actuated. In such way, the detection result of the sensor 23 is not adversely affected. Moreover, the actuator 24 covers the bottom of the second compartment 213 and is actuated to generate the flow of gas. The gas is transported through the outlet aperture 216 of the second compartment 213, and then the gas is transported through the opening 221 of the carrying plate 22 and discharged from the compartment body 21. That is, the gas is transported and then discharged into the environment outside the compartment body 21 via the outlet aperture 216 and the opening 221.

Please refer to FIGS. 3A to 3C again. In an embodiment, the carrying plate 22 may be a circuit board and includes a connector 222 disposed thereon for allowing a flexible circuit board (not shown) to be inserted thereinto. Consequently, the carrying plate 22 is electrically connected to and in signal communication with the flexible circuit board through the connector 222.

Figure 4A:
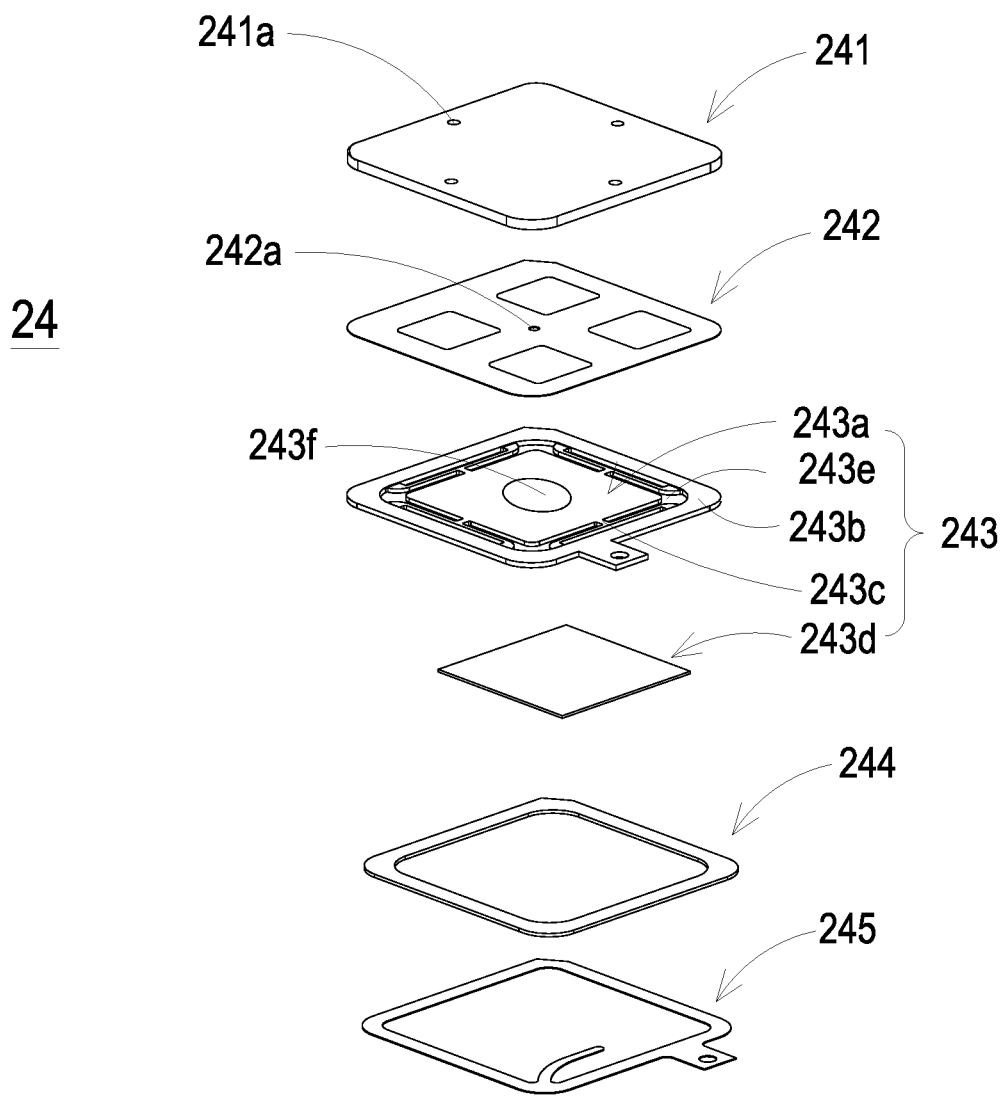
FIG. 4A is a schematic exploded view illustrating the actuator of the gas sensing module of the gas detecting device according to the embodiment of the present disclosure.
Figure 4B:
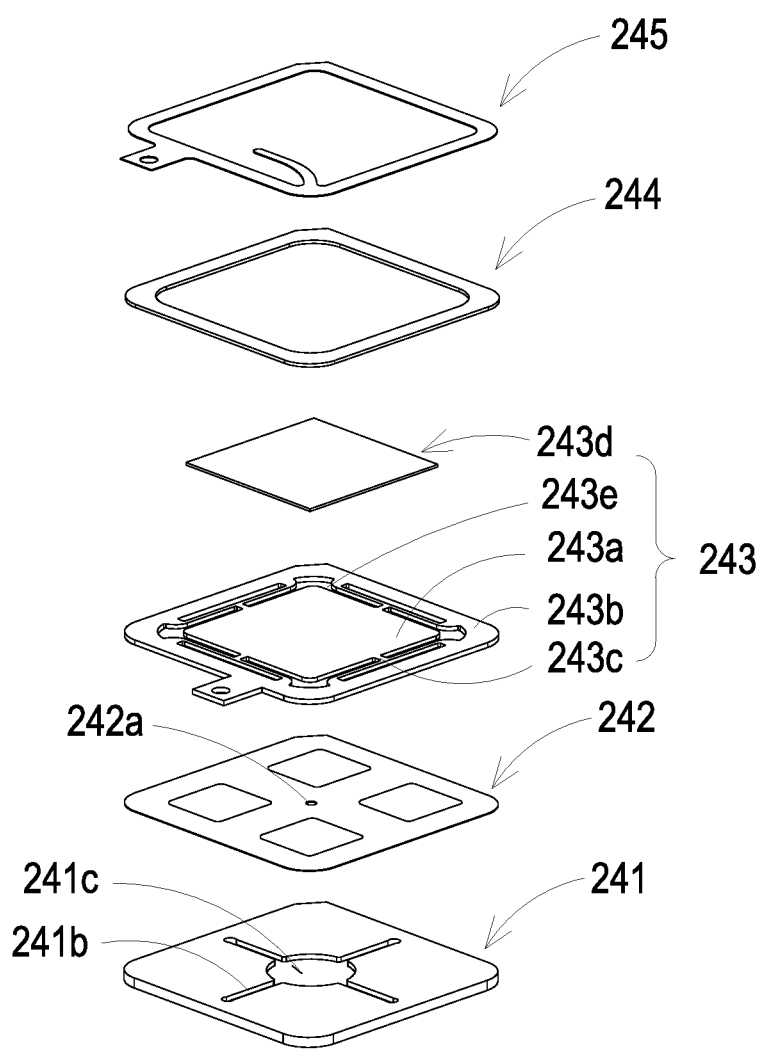
FIG. 4B is a schematic exploded view illustrating the actuator of FIG. 4A and taken along another viewpoint.
Figure 5A:
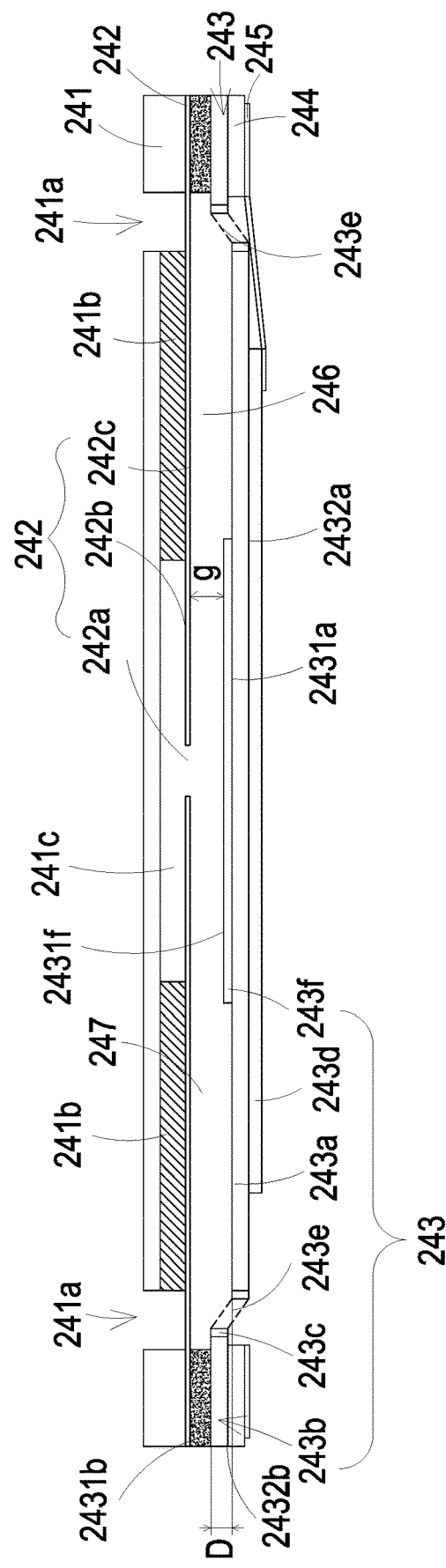
FIG. 5A is a schematic cross-sectional view illustrating the actuator of FIG. 4A.

Please refer to FIGS. 4A, 4B and 5A. In an embodiment, the actuator 24 is a gas pump. The actuator 24 includes a gas inlet plate 241, a resonance plate 242, a piezoelectric actuator 243, an insulation plate 244 and a conducting plate 245, which are stacked on each other sequentially. The gas inlet plate 241 has at least one inlet aperture 241a, at least one convergence channel 241b and a convergence chamber 241c. The number of the inlet aperture 241a is the same as the number of the convergence channel 241b. In this embodiment, the number of the inlet apertures 241a and the convergence channels 241b is exemplified by four for each but not limited thereto. The four inlet apertures 241a penetrate through the four convergence channels 241b respectively, and the four convergence channels 241b converge to the convergence chamber 241c.

The resonance plate 242 is assembled on the gas inlet plate 241 by attaching. The resonance plate 242 has a central aperture 242a, a movable part 242b and a fixed part 242c. The central aperture 242a is located in the center of the resonance plate 242 and is aligned with the convergence chamber 241c of the gas inlet plate 241. The region of the resonance plate 242 around the central aperture 242a and corresponding to the convergence chamber 241c is the movable part 242b. The region of the periphery of the resonance plate 242 securely attached on the gas inlet plate 241 is the fixed part 242c.

The piezoelectric actuator 243 includes a suspension plate 243a, an outer frame 243b, at least one connection component 243c, a piezoelectric element 243d, at least one vacant space 243e and a bulge 243f. The suspension plate 243a is square, and has a first surface 2431a and a second surface 2432a. The first surface 2431a and the second surface 2432a are opposed to each other. The outer frame 243b is disposed around the periphery of the suspension plate 243a. The outer frame 243b has a coupling surface 2431b and a bottom surface 2432b opposite to the coupling surface 2431b. The at least one connection component 243c is connected between the suspension plate 243a and the outer frame 243b for elastically supporting the suspension plate 243a. The at least one vacant space 243e is formed among the suspension plate 243a, the outer frame 243b and the at least one connection component 243c for allowing the gas to flow through. The bulge 243f is formed on the first surface 2431a of the suspension plate 243a. In this embodiment, the formation of the bulge 243f may be completed by using an etching process, in which the region between the periphery of the bulge 243f and the periphery of the suspension plate 243a is partially removed. Accordingly, the bulge 243f of the suspension plate 243a is higher than the first surface 2431a, and a stepped structure is formed.

As shown in FIG. 5A, in this embodiment, the suspension plate 243a may be processed by a stamping method, by which the outer frame 243b, the connection component 243c, and the suspension plate 243a have a concave profile in cross section. The stamping method makes the suspension plate 33a disposed further away from the resonance plate 32 a distance D, which can be adjusted by the at least one connection component 243c formed between the suspension plate 243a and the outer frame 243b. Consequently, the top surface 2431f of the bulge 243f and the first surface 2431a of the suspension plate 243a are not coplanar with the coupling surface 2431b of the outer frame 243b. Namely, the top surface 2431f of the bulge 243f and the first surface 2431a are lower than the coupling surface 2431b of the outer frame 243b, and the second surface 2432a of the suspension plate 243a is lower than the bottom surface 2432b of the outer frame 243b. In the embodiment, the piezoelectric element 243d is attached on the second surface 2432a of the suspension plate 243a and aligned with the bulge 243f. In response to an applied voltage, the piezoelectric element 243d is deformed by the piezoelectric effect to drive the suspension plate 243a to undergo the bending vibration. By utilizing a small amount of adhesive applied to the coupling surface 2431b of the outer frame 243b, the piezoelectric actuator 243 is attached to the fixed part 242c of the resonance plate 242 after heat pressing, thereby assembling the piezoelectric actuator 243 and the resonance plate 242 in combination. In addition, the insulation plate 244 and the conducting plate 245 are both thin frame-shaped sheets, which are sequentially stacked under the piezoelectric actuator 243. In the embodiment, the insulation plate 244 is attached to the bottom surface 2432b of the outer frame 243b of the piezoelectric actuator 243.

Please refer to FIG. 5A again. After the gas inlet plate 241, the resonance plate 242, the piezoelectric actuator 243, the insulation plate 244 and the conducting plate 245 of the actuator 24 are stacked and assembled sequentially, a chamber gap g is formed between the first surface 2431a of the suspension plate 243a and the resonance plate 242. Since the distance between the suspension plate 243a and the resonance plate 242 will influence the transportation effect of the actuator 24, it is very important to maintain the chamber gap g for providing a stable transportation efficiency of the actuator 24. The suspension plate 243a of the actuator 24 is processed by the stamping method as described above, and it makes the suspension plate 243a disposed further away from the resonance plate 32. Consequently, the first surface 2431a of the suspension plate 243a and the coupling surface 2431b of the outer frame 243b are non-coplanar. Namely, the top surface 2431f and the first surface 2431a of the suspension plate 243a are lower than the coupling surface 2431b of the outer frame 243b, and the second surface 2432a of the suspension plate 243a is lower than the bottom surface 2432b of the outer frame 243b. In this way, the entire structure may be improved by adopting the stamping method to process the suspension plate 243a. The space between the suspension plate 243a of the piezoelectric actuator 243 and the resonance plate 242 is adjustable due to the stamping method, by which the adjustable chamber gap g is realized. That is, the design of a chamber space 246 is improved by processing the suspension plate 243a of the piezoelectric actuator 243 to be disposed further away from the resonance plate 242. The desired chamber gap g can be satisfied by simply adjusting the distance D, as described above. It simplifies the structural design regarding the adjustment of the chamber gap g, and it also achieves the advantages of simplifying the process and shortening the processing time.

Figure 5B:
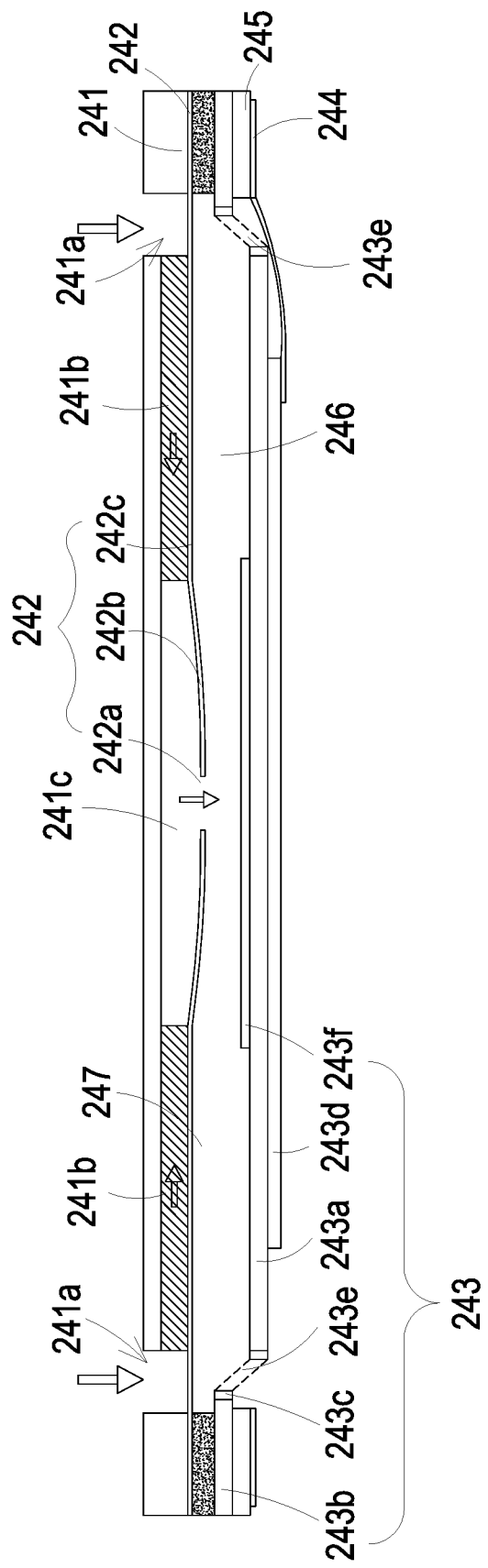
FIGS. 5B, 5C and 5D schematically illustrate the actions of the actuator of FIG. 5A.
Figure 5C:
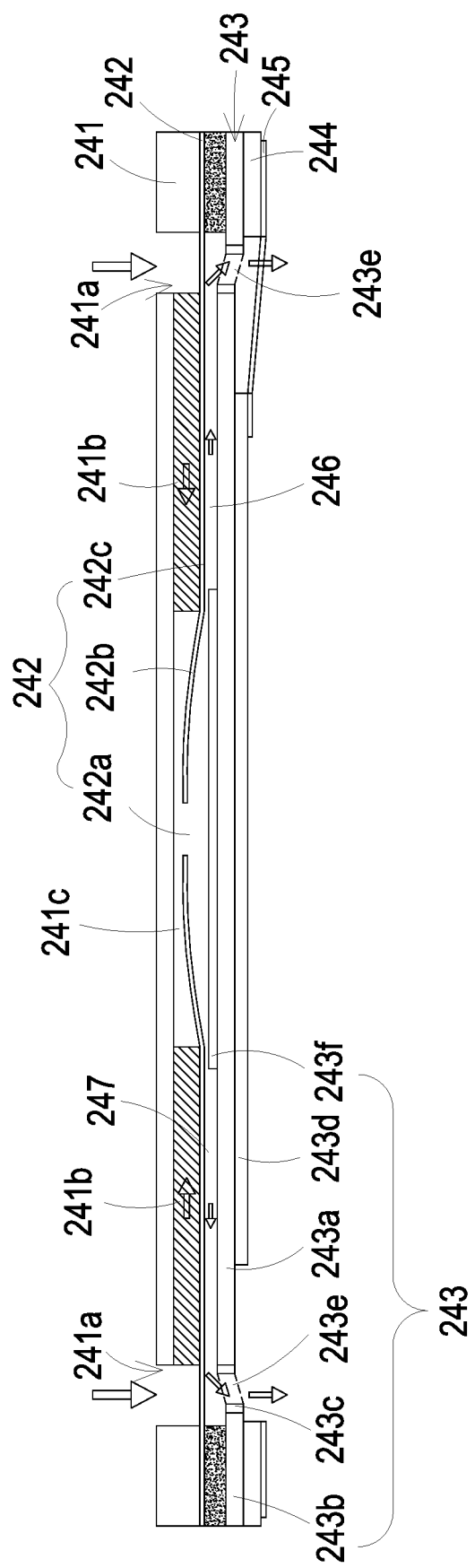
Figure 5D:
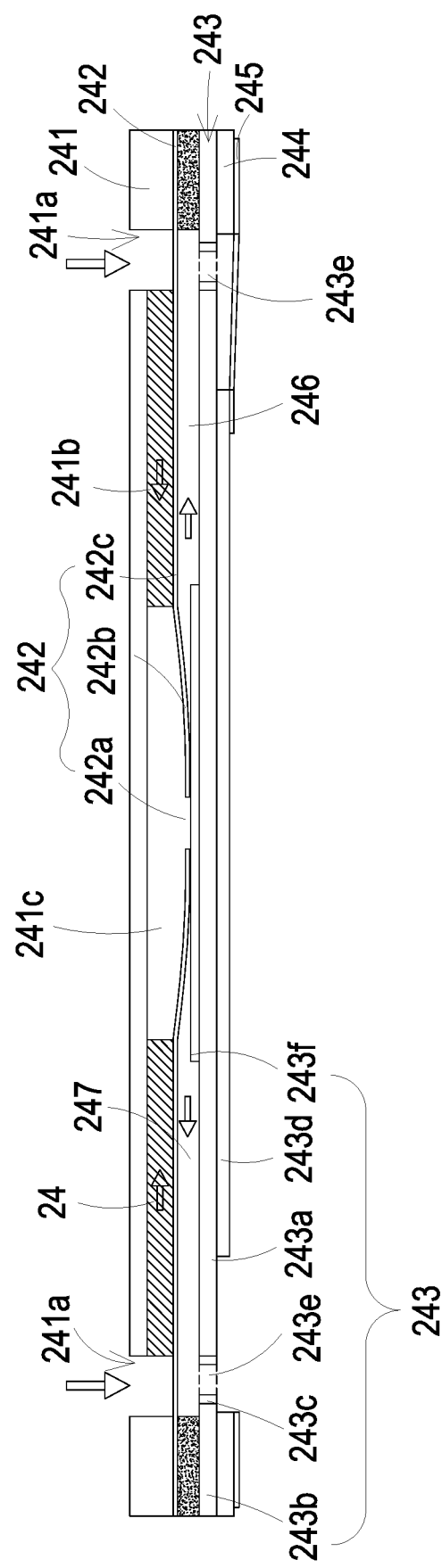

FIGS. 5B and 5D are schematic views illustrating actions of the actuator of FIG. 5A. Please refer to FIG. 5B firstly. When the piezoelectric element 243d of the piezoelectric actuator 243 is deformed in response to an applied voltage, the suspension plate 243a is driven to displace in the direction away from the gas inlet plate 241. In that, the volume of the chamber space 246 is increased, a negative pressure is formed in the chamber space 246, and the gas in the convergence chamber 241c is inhaled into the chamber space 246. At the same time, the resonance plate 242 is in resonance and thus displaced synchronously in the direction away from the gas inlet plate 241. Thereby, the volume of the convergence chamber 241c is increased. Since the gas in the convergence chamber 241c flows into the chamber space 246, the convergence chamber 241c is also in a negative pressure state, and the gas is sucked into the convergence chamber 241c by flowing through the inlet aperture 241a and the convergence channel 241b. Please refer to FIG. 5C, the piezoelectric element 243d drives the suspension plate 243a to be displaced toward the gas inlet plate 241 to compress the chamber space 246. Thus, the gas contained in the chamber space 246 is transported to flow through the vacant spaces 243e in the direction away from the gas inlet plate 241 and it achieves the effect of gas transportation. Similarly, the resonance plate 242 is actuated in resonance by the suspension plate 243a and displaced toward the gas inlet plate 241. Thus, the gas contained in convergence chamber 241c is compressed synchronously to flow to the chamber space 246. Finally, as shown in FIG. 5D. When the suspension plate 243a is driven to displace in the direction away from the gas inlet plate 241, the resonance plate 242 is also driven to displace in the direction away from the gas inlet plate 241 at the same time. In that, the resonance plate 242 pushes the gas in the chamber space 246 toward the vacant space 243e, and the volume of the convergence chamber 241c is increased. Thus, the gas can continuously flow through the inlet aperture 241a and the convergence channel 241b and be converged in the convergence chamber 241c. By repeating the actions shown in the above continuously, the actuator 24 can continuously inhale the gas through the inlet aperture 241a and transport the gas through the vacant spaces 243e in the direction away from the gas inlet plate 241. It achieves the effect of transporting the gas to the sensor 23 for detecting, thereby improving the detecting efficiency.

Please refer to FIG. 5A again. In another embodiment, the actuator 24 can be a micro-electromechanical-systems gas pump formed by a micro-electromechanical-systems method. The gas inlet plate 241, the resonance plate 242, the piezoelectric actuator 243, the insulation plate 244, and the conducting plate 245 can all be made through a surface micromachining technique to reduce the volume of the actuator 24.

Figure 6:
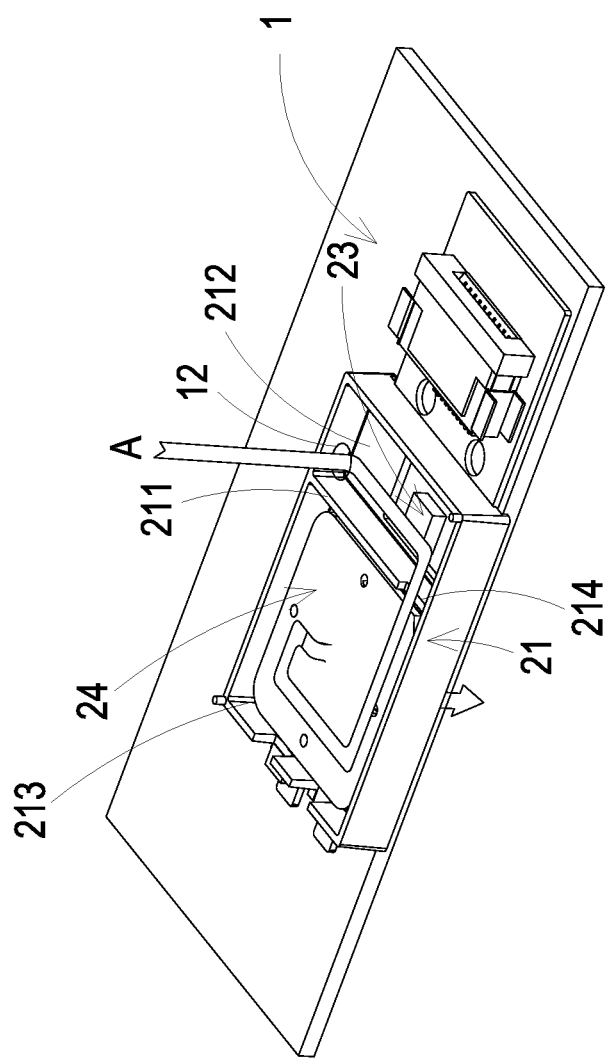
FIG. 6 schematically illustrates the flowing direction of the gas in the gas sensing module of the gas detecting device according to the embodiment of the present disclosure.
Figure 7:
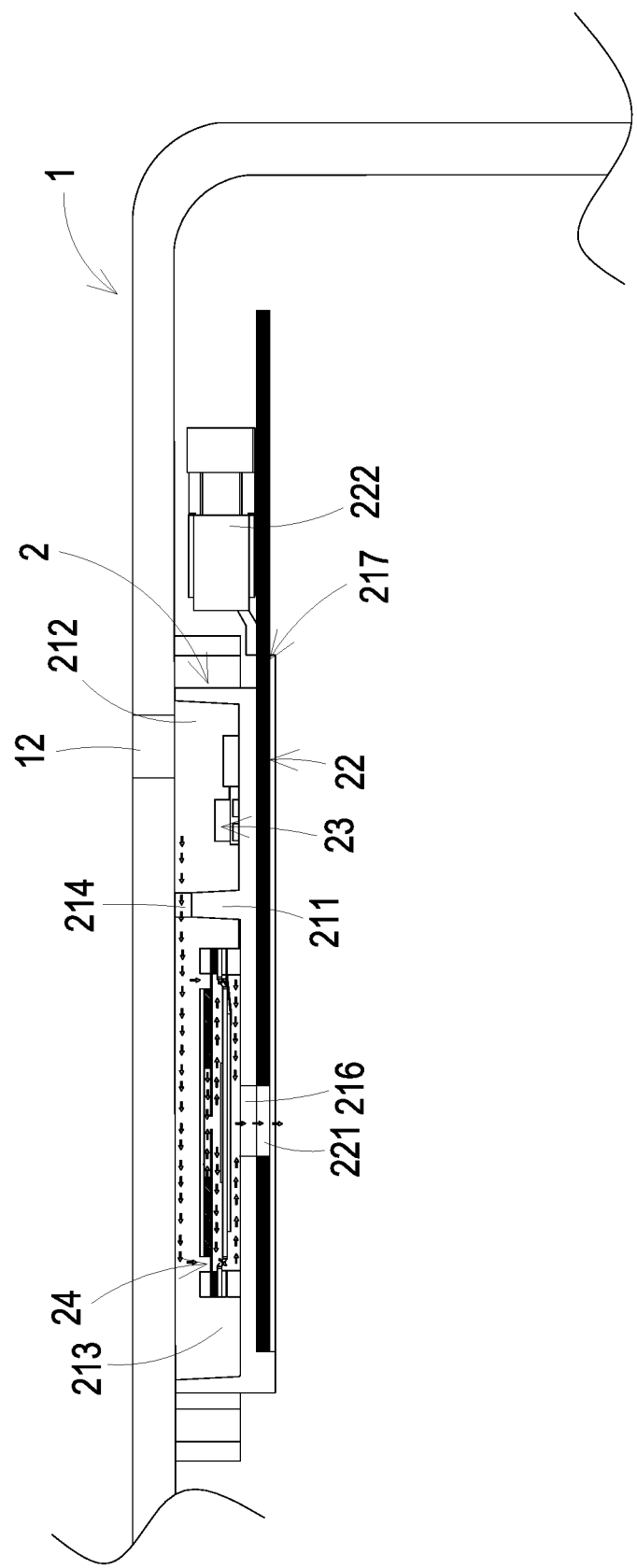
FIG. 7 is an enlarged fragmentary side view illustrating the flowing direction of the gas in the gas sensing module of the gas detecting device according to the embodiment of the present disclosure.

Please refer to FIGS. 6 and 7. The gas sensing module 2 is embedded in the chamber 11 of the main body 1. FIG. 6 schematically illustrates the flowing direction of the gas in the gas sensing module 2 disposed in the main body 1. For ease of discussion, the main body 1 is not clearly shown. The first inlet 12 of the main body 1 is aligned with the first compartment 212 of the compartment body 21. The first inlet 12 of the main body 1 and the sensor 23 within the first compartment 212 are not aligned with each other. That is, the first inlet 12 is not disposed directly above the sensor 23, and the first inlet 12 and the sensor 23 are misaligned with each other. When the actuator 24 is actuated, a negative pressure is formed in the second compartment 213, so that the ambient gas around the main body 1 is inhaled into the first compartment 212 through the first inlet 12 and the sensor 23 within the first compartment 212 measures the gas flowing through the surface of the sensor 23 so as to monitor air quality around the main body 1. As the actuator 24 is actuated continuously, the gas is transported to the second compartment 213 through the notch 214 of the partition plate 211, and then the gas is discharged from the compartment body 21 through the outlet aperture 216 and the opening 221 of the carrying plate 22. In such way, the gas is guided along a single direction A (illustrated in FIG. 6).

In this embodiment, the sensor 23 can be at least one selected from the group consisting of an oxygen sensor, a carbon monoxide sensor, a carbon dioxide sensor, a temperature sensor, an ozone sensor, a volatile organic compound sensor and combinations thereof. In some embodiments, the sensor 23 can be at least one selected from the group consisting of a bacterial sensor, a virus sensor, a microorganism sensor and combinations thereof.

From the above descriptions, the gas sensing module 2 of the gas detecting device is capable of monitoring the air quality in the environment in any time. As the actuator 24 is actuated, the gas is guided into the interior of the gas sensing module 2 rapidly and stably, so that the sensing efficacy of the sensor 23 is enhanced. Since the sensor 23 in the first compartment 212 and the actuator 24 in the second compartment 213 are separated from each other by the partition plate 211, the heat generated from the actuator 24 is blocked by the partition plate 211. In such way, the detection result of the sensor 23 is not adversely affected by the heat and other components within the gas detecting device. In other words, the gas detecting device can monitor the air quality in the environment rapidly and accurately at anytime and anywhere.

Figure 8:
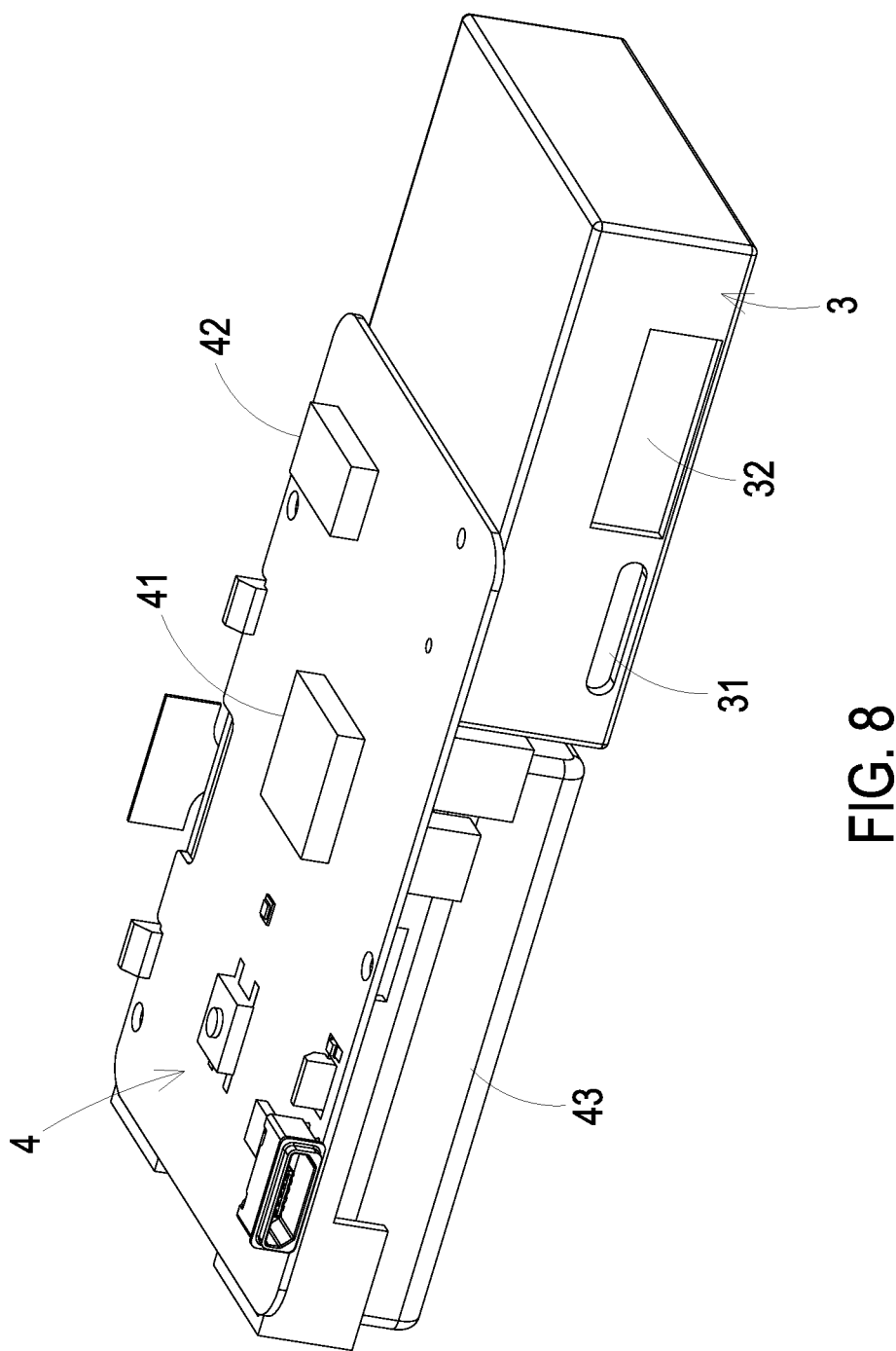
FIG. 8 is a schematic perspective view illustrating a particulate measuring module and a control module of the gas detecting device according to the embodiment of the present disclosure.

FIG. 8 is a schematic perspective view illustrating a particulate measuring module and a control module of the gas detecting device according to the embodiment of the present disclosure. In an embodiment, the gas detecting device further includes a particulate measuring module 3 for detecting the particulates in the gas. The particulate measuring module 3 is disposed in the chamber 11 of the main body 1. As shown in FIG. 8, the particulate measuring module 3 includes an inlet channel 31, an outlet channel 32 and a particulate detector (not shown). The particulate detector is disposed within the particulate measuring module 3. The inlet channel 31 is aligned with the second inlet 13 of the main body 1. The outlet channel 32 is aligned with the outlet 14 of the main body 1. After the ambient gas is introduced into the particulate measuring module 3 through the inlet channel 31, the concentration of the particulates in the gas is measured by the particulate detector. Then, the gas is discharged from the outlet channel 32 and finally discharged through the outlet 14 into the environment outside the main body 1. In this embodiment, the particulate detector may be a PM2.5 sensor.

Figure 9:
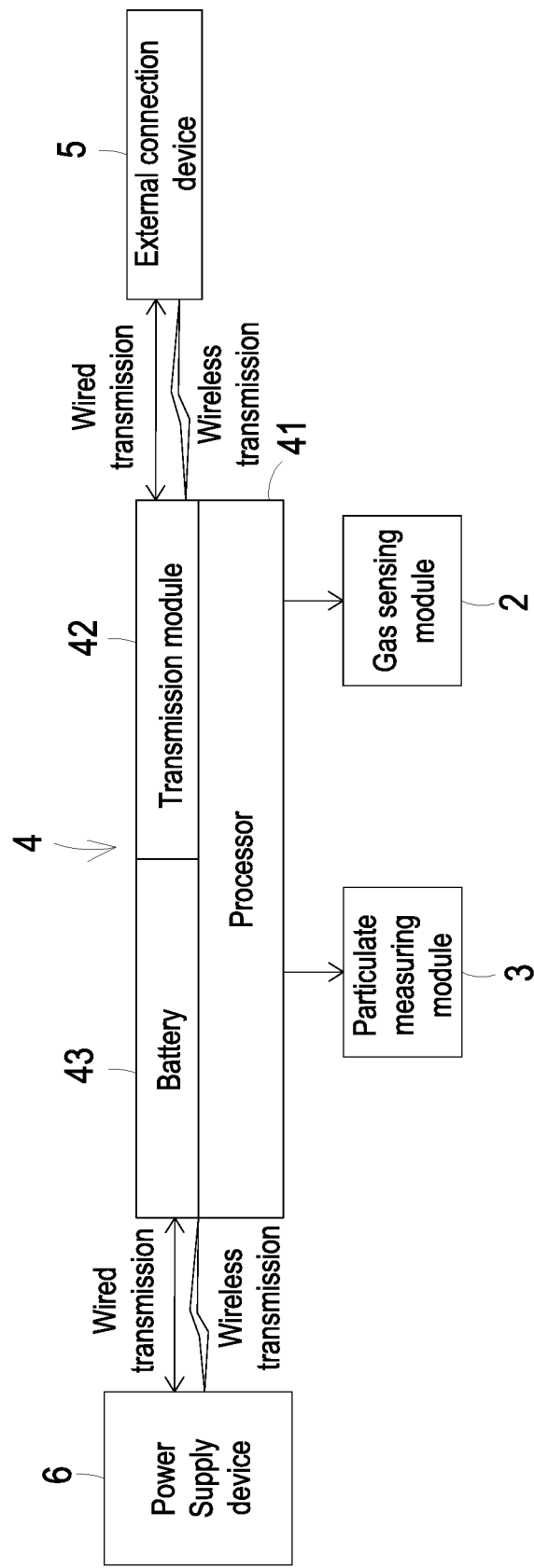
FIG. 9 is a functional block diagram illustrating the architecture of gas detecting device according to the embodiment of the present disclosure.

Please refer to FIGS. 8 and 9. In this embodiment, the control module 4 further includes a processor 41 and a transmission module 42. The processor 41 is electrically connected to the transmission module 42, the gas sensing module 2 and the particulate measuring module 3 for controlling actuations of the transmission module 42, the sensor 23 and the actuator 24 of the gas sensing module 2, and the particulate detector of the particulate measuring module 3. The processor 41 analyzes detecting results from the sensor 23 and the particulate detector, and converters the analysis result into a monitoring value to be stored. The transmission module 42 transmits the monitoring value to an external connection device 5 for storage. The external connection device 5 may be at least one selected from the group consisting of a cloud system, a portable electronic device, a computer system, a display device and combinations thereof. The external connection device 5 is configured to display information carried by the monitoring value and announce an alert.

In this embodiment, the transmission module 42 transmits the monitoring value to the external connection device 5 via a wired transmission technology or a wireless transmission technology. The transmission module 42 is a wired transmission module, which may be at least one selected from the group consisting of a USB (Universal Serial Bus) transmission module, a mini-USB transmission module (see the reference number C of FIG. 1D), a micro-USB transmission module and combinations thereof. Alternatively, the transmission module 42 is a wireless transmission module, which may be at least one selected from the group consisting of a Wi-Fi transmission module, a Bluetooth transmission module, a radio frequency identification (RFID) transmission module, a near field communication (NFC) transmission module and combinations thereof. The control module 4 further includes a battery 43. The battery 43 is configured to store and output the electric energy. Moreover, the battery 43 can be connected to a power supply device 6 for receiving and storing the electric energy from the power supply device 6. The battery 43 provides the processor 41 with the electric energy, and the processor 41 issues electric signal and driving signal to control actuations of the gas sensing module 2 and the particulate measuring module 3. The electric energy from the power supply device 6 is transmitted to the battery 43 via the wired transmission technology or the wireless transmission technology.

From the above descriptions, the present disclosure provides the gas detecting device. The gas sensing module of the gas detecting device is capable of monitoring the air quality in the environment at any time. When the actuator is actuated, the gas is guided into the interior of the gas sensing module quickly and stably, so that the efficacy of the gas sensing module is enhanced. Moreover, the actuator in the second compartment and the sensor in the first compartment are separated from each other by the partition plate, the heat generated from the actuator is blocked by the partition plate to reduce the influence on the sensor while the sensor monitors the air quality. In such way, the detection result of the sensor is not adversely affected by the heat and other components (e.g., the control module) within the gas detecting device. Consequently, the gas detecting device can monitor the air quality in the environment rapidly and accurately at anytime and anywhere. Furthermore, the gas detecting device further includes a particulate measuring module for measuring the concentration of the particulates in the gas from the external environment and transmitting the monitoring value to the external connection device. The external connection device can obtain the information carried by the monitoring value and announce an alert to the user in the environment immediately so that the user can take preventive measures or escape immediately, and the influence and injury to the human health caused by the gas exposure in the environment will be prevented.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device, comprising:
a main body having a portable size defined by a length, a width and a height, and having a chamber, a first inlet, a second inlet and an outlet, wherein the chamber is formed within the main body, and the first inlet, the second inlet and the outlet are in fluid communication with the chamber;
a gas sensing module comprising a compartment body, a carrying plate, a sensor and an actuator, wherein the compartment body is located under the first inlet of the main body and has a partition plate disposed therein to divide an interior of the compartment body into a first compartment and a second compartment, and the partition plate has a notch for allowing the first compartment and the second compartment to be in fluid communication with each other, wherein the first compartment has an opening, the second compartment has an outlet aperture, the carrying plate is assembled on a bottom of the compartment body and is packaged on and electrically connected to the sensor, the sensor penetrates the opening and is disposed within the first compartment, the actuator is disposed within the second compartment, and the actuator and the sensor are separated from each other, wherein the actuator is actuated to introduce ambient gas into the gas sensing module through the first inlet, and the gas is measured by the sensor and discharged from the outlet aperture of the second compartment;
a particulate measuring module disposed within the chamber of the main body, and comprising an inlet channel, an outlet channel and a particulate detector, wherein the particulate detector is disposed within the particulate measuring module, the inlet channel is aligned with the second inlet of the main body, and the outlet channel is aligned with the outlet of the main body, wherein the gas is introduced into the particulate measuring module through the inlet channel, a concentration of particulates in the gas is measured by the particulate detector and the gas is discharged from the outlet channel; and
a control module configured to control actuations of the gas sensing module and the particulate measuring module, and convert detection results of the gas sensing module and the particulate measuring module into a monitoring value to be stored and transmitted to an external connection device for storage.

2. The gas detecting device according to claim 1, wherein the length of the main body is in a range between 92 mm and 102 mm, the width of the main body is in a range between 41 mm and 61 mm, and the height of the main body is in a range between 19 mm and 23 mm so as to form the portable size.

3. The gas detecting device according to claim 2, wherein the length of the main body is 97 mm, the width of the main body is 51 mm, and the height of the main body is 21 mm.

4. The gas detecting device according to claim 1, wherein the bottom of the compartment body has an accommodation recess for allowing the carrying plate to be partially received and positioned within so that the bottom of the compartment body is covered by the carrying plate, wherein the carrying plate has an opening aligned with the outlet aperture of the second compartment so that the gas is discharged from the compartment body through the outlet aperture of the second compartment and the opening of the carrying plate.

5. The gas detecting device according to claim 1, wherein the sensor is a gas sensor.

6. The gas detecting device according to claim 5, wherein the gas sensor is at least one selected from a group consisting of an oxygen sensor, a carbon monoxide sensor, a carbon dioxide sensor, and combinations thereof.

7. The gas detecting device according to claim 5, wherein the gas sensor is a volatile organic compound sensor.

8. The gas detecting device according to claim 1, wherein the sensor is at least one selected from a group consisting of a bacterial sensor, a virus sensor, a microorganism sensor, and combinations thereof.

9. The gas detecting device according to claim 1, wherein the actuator is a micro-electromechanical-systems gas pump.

10. The gas detecting device according to claim 1, wherein the actuator is a gas pump, and the gas pump comprises:
a gas inlet plate having at least one inlet aperture, at least one convergence channel and a convergence chamber, wherein the at least one inlet aperture allows the gas to flow in, and the at least one convergence channel is aligned with the at least one inlet aperture and guides the gas from the inlet aperture toward the convergence chamber;
a resonance plate having a central aperture and a movable part, wherein the central aperture is aligned with the convergence chamber and the movable part surrounds the central aperture; and
a piezoelectric actuator aligned with the resonance plate;
wherein a chamber space is formed between the resonance plate and the piezoelectric actuator, so that the gas from the at least one inlet aperture of the gas inlet plate is converged to the convergence chamber along the at least one convergence channel and flows into the chamber space through the central aperture of the resonance plate when the piezoelectric actuator is driven, whereby the gas is further transported through a resonance between the piezoelectric actuator and the movable part of the resonance plate.

11. The gas detecting device according to claim 10, wherein the piezoelectric actuator comprises:
a suspension plate having a first surface, a second surface and a bulge, wherein the bulge is disposed on the first surface;
an outer frame arranged around the suspension plate and having a coupling surface;
at least one connection component connected between the suspension plate and the outer frame for elastically supporting the suspension plate; and
a piezoelectric element attached on the second surface of the suspension plate to drive the suspension plate to undergo the bending vibration in response to an applied voltage;
wherein the at least one connection component is formed between the suspension plate and the outer frame, the first surface of the suspension plate and the coupling surface of the outer frame are non-coplanar, and a chamber gap is maintained between the first surface of the suspension plate and the resonance plate.

12. The gas detecting device according to claim 10, wherein the gas pump comprises a conducting plate and an insulation plate, and the gas inlet plate, the resonance plate, the piezoelectric actuator, the insulation plate and the conducting plate are stacked sequentially.

13. The gas detecting device according to claim 1, wherein the control module comprises a processor and a transmission module, wherein the processor controls actuations of the transmission module, the sensor of the gas sensing module and the particulate detector of the particulate measuring module, the processor analyzes and converts the detection results of the sensor and the particulate detector into the monitoring value, and the transmission module transmits the monitoring value to the external connection device for storage.

14. The gas detecting device according to claim 1, wherein the external connection device is at least one selected from the group consisting of a cloud system, a portable device, a computer system, and combinations thereof.

15. The gas detecting device according to claim 13, wherein the control module further comprises a battery configured to store and output electric power, the battery is electrically connected to a power supply device for receiving and storing electric power from the power supply device, the battery provides the processor with the electric power, and the processor provides the gas sensing module and the particulate measuring module with electric signal and driving signal.

16. The gas detecting device according to claim 1, wherein the particulate detector is a PM2.5 sensor.

17. A gas detecting device, comprising:
at least one main body having a portable size defined by at least one length, at least one width and at least one height, and having at least one chamber, at least one first inlet, at least one second inlet and at least one outlet, wherein the chamber is formed within the main body, and the first inlet, the second inlet and the outlet are in fluid communication with the chamber;
at least one gas sensing module comprising at least one compartment body, at least one carrying plate, at least one sensor and at least one actuator, wherein the compartment body is located under the first inlet of the main body and has at least one partition plate disposed therein to divide an interior of the compartment body into at least one first compartment and at least one second compartment, and the partition plate has at least one notch for allowing the first compartment and the second compartment to be in fluid communication with each other, wherein the first compartment has at least one opening, the second compartment has at least one outlet aperture, the carrying plate is assembled on a bottom of the compartment body and is packaged on and electrically connected to the sensor, the sensor penetrates the opening and is disposed within the first compartment, the actuator is disposed within the second compartment, and the actuator and the sensor are separated from each other, wherein the actuator is actuated to introduce ambient gas into the gas sensing module through the first inlet, and the gas is measured by the sensor and discharged from the outlet aperture of the second compartment;
at least one particulate measuring module disposed within the chamber of the main body, and comprising at least one inlet channel, at least one outlet channel and at least one particulate detector, wherein the particulate detecule, the inlet channel is aligned with the second inlet of the main body, and the outlet channel is aligned with the outlet of the main body, wherein the gas is introduced into the particulate measuring module through the inlet channel, a concentration of particulates in the gas is measured by the particulate detector and the gas is discharged from the outlet channel; and at least one control module configured to control actuations of the gas sensing module and the particulate measuring module, and convert detection results of the gas sensing module and the particulate measuring module into a monitoring value to be stored and transmitted to at least one external connection device for storage.

\* \* \* \* \*